United States Patent [19]

Kruse et al.

[11] Patent Number: 4,624,963
[45] Date of Patent: Nov. 25, 1986

[54] USE OF OXINDOLE COMPOUNDS FOR THE TREATMENT OF EPILEPSY

[75] Inventors: Hansjörg Kruse; Heinz Kuch, both of Kelkheim, Fed. Rep. of Germany

[73] Assignee: Hoechst Aktiengesellschaft, Fed. Rep. of Germany

[21] Appl. No.: 721,400

[22] Filed: Apr. 9, 1985

[30] Foreign Application Priority Data

Apr. 11, 1984 [DE] Fed. Rep. of Germany ....... 3413572

[51] Int. Cl.⁴ .................. A61K 31/40; A61K 31/445; A61K 31/495; A61K 31/535
[52] U.S. Cl. .................................... 514/418; 514/227; 514/255; 514/340; 514/422
[58] Field of Search ................. 598/492, 489; 514/418, 514/422, 340, 227, 255

[56] References Cited

U.S. PATENT DOCUMENTS 4,542,148 9/1985 Kuch et al. .................... 514/418

FOREIGN PATENT DOCUMENTS 0062887 10/1982 European Pat. Off. ............ 548/486
3114351 11/1982 Fed. Rep. of Germany .

Primary Examiner—Richard L. Raymond
Assistant Examiner—D. B. Springer
Attorney, Agent, or Firm—Finnegan, Henderson, Farabow, Garrett & Dunner

[57] ABSTRACT

Oxindole compounds of the formula I

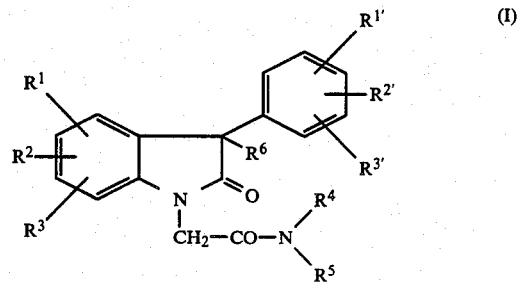

in which $R^1$, $R^2$, $R^3$, $R^{1'}$, $R^{2'}$, $R^{3'}$, $R^4$, $R^5$ and $R^6$ have the meanings given, and physiologically acceptable salts thereof, for the treatment of epilepsy and their use for the preparation of a medicament for the treatment of epilepsy are described.

3 Claims, No Drawings

USE OF OXINDOLE COMPOUNDS FOR THE TREATMENT OF EPILEPSY

Oxindole compounds with a neuro-anabolic (psychotropic) action are known from DE-A-3,114,351 (corresponding to EP-A-62,887 and U.S. patent application Ser. No. 366,321, now U.S. Pat. No. 4,452,148). Surprisingly, it has now been found that some of these compounds have an antiepileptic (anticonvulsive) action.

The invention therefore relates to oxindole compounds of the formula I

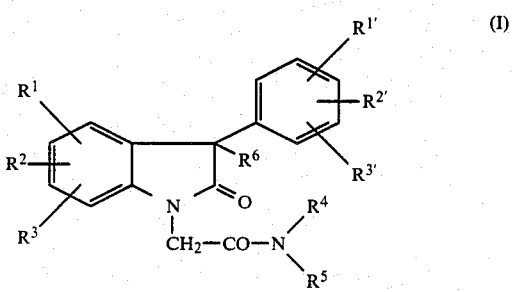

for the treatment of epilepsy.

In formula I $R^1$, $R^2$, $R^3$, $R^{1'}$, $R^{2'}$ and $R^{3'}$ are identical or different and independently of one another denote hydrogen, halogen, such as fluorine, chlorine or bromine, or straight-chain or branched alkyl with 1 to 4 carbon atoms, $R^4$ and $R^5$ are identical or different and independently of one another denote hydrogen or straight-chain or branched alkyl with 1 to 4 carbon atoms; cyclohexyl, alkylcyclohexyl with 1 to 4 carbon atoms in the alkyl part, cycloheptyl or cyclooctyl; phenyl, which can be mono- or di-substituted by halogen, such as fluorine, chlorine or bromine, straight-chain or branched alkyl with 1 to 4 carbon atoms, trifluoromethyl, methylenedioxy or alkoxy with 1 to 3 carbon atoms; or phenylalkyl with 1 to 3 carbon atoms in the alkyl part, it being possible for the phenyl nucleus to be substituted as indicated above for phenyl, or hydroxyalkyl with 1 to 4 carbon atoms, or $R^4$ and $R^5$, together with the nitrogen atom carrying them, denote pyrrolidino, piperidino, morpholino or phenylpiperazino, it being possible for the phenyl nucleus to be substituted as indicated above for phenyl, and $R^6$ denotes hydrogen, alkyl with 1, 2 or 3 carbon atoms or hydroxyl.

Compounds of the formula I which are particularly preferred for the treatment of epilepsy are those in which $R^{1'}$, $R^{2'}$ and $R^{3'}$ denote hydrogen, $R^1$ denotes hydrogen or chlorine in the 5-position of the indole, $R^2$ and $R^3$ denote hydrogen, $R^4$ and $R^5$ are identical or different and independently of one another denote hydrogen, alkyl with 1, 2 or 3 carbon atoms, cyclohexyl, methylcyclohexyl, cycloheptyl, cyclooctyl, hydroxyalkyl with 2 or 3 carbon atoms or benzyl or phenethyl, it being possible for the phenyl radicals in each case to be mono- or di-substituted in the phenyl nucleus by halogen, such as fluorine or chlorine, methylenedioxy or alkoxy with 1, 2 or 3 carbon atoms, or $R^4$ and $R^5$, together with the nitrogen atom carrying them, denote piperidino, pyrrolidino, morpholino or N-phenylpiperazino, it being possible for the phenyl nucleus to be mono- or di-substituted by fluorine or chlorine, methylenedioxy or alkoxy with 1, 2 or 3 carbon atoms, and $R^6$ denotes hydrogen, methyl or hydroxyl.

The compounds of the formula I to be used according to the invention have an asymmetric carbon atom and therefore occur in stereoisomeric forms. The invention relates to the use of the racemic mixtures and of the dextrorotatory and levorotatory enantiomers.

Where the compounds to be used according to the invention have a basic character, the invention also relates to their salts with pharmaceutically acceptable acids, such as, for example, with hydrogen halide acids, in particular hydrochloric acid, acetic acid, malic acid, tartaric acid, maleic acid, fumaric acid, methanesulfonic acid and the like.

The compound of the formula I in which the radicals $R^1$ to $R^6$, $R^{1'}$, $R^{2'}$ and $R^{3'}$ denote hydrogen (2-oxo-3-phenyl-1-indolineacetamide, formula II)

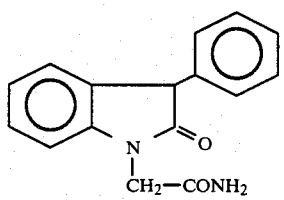

is of very particular importance for the treatment of epilepsy.

The compounds of the formula I to be used according to the invention can be prepared by the processes described in DE-A-3,114,351 (corresponding to EP-A-62,887 and U.S. patent application Ser. No. 366,321, now U.S. Pat. No. 4,452,148).

The invention furthermore relates to the use of the compounds of the formula I and of salts thereof for the preparation of a medicament for the treatment of epilepsy.

The compounds of the formula I or II which are suitable for the treatment of epilepsy or their salts are advantageously processed to pharmaceutical products in the customary manner. For peroral use, the compounds of the formula I or II can be processed to tablets, coated tablets or capsules, which, if appropriate, contain customary pharmaceutical excipients, diluents and/or auxiliaries, in addition to the active compounds. The active compound content is 1 to 95 percent, preferably 10 to 80 percent. Examples of suitable excipients, diluents and auxiliaries are calcium carbonate, calcium phosphate, sodium phosphate, lactose, corn starch, alginates, gelatin, aluminum stearate, magnesium stearate, talc or silicone oil.

Such a medicament can advantageously be formulated in dosage units suited to the desired therapy.

Such medicaments can contain 1 to 1,000 mg, advantageously 5 to 500 mg, of a compound of the formula I, as the active compound, per individual dose.

For parenteral administration, the active compound can be used as injectable aqueous or oily suspensions, which can additionally also contain suspending agents, such as, for example, sodium carboxymethylcellulose, methylcellulose, hydroxypropylcellulose, sodium alginate or polyvinylpyrrolidone, dispersants, such as polyoxyethylene stearate, and preservatives; groundnut oil, olive oil, coconut oil, sesame oil or paraffin oil can be used for the oily suspensions.

The oxindole compounds of the formula I are highly effective in test models which suggest an antiepileptic action in humans and other mammals. Thus, they prevent the development of tonic and clonic spasms which can be triggered off by a number of methods, thus, for example, by electric shock, pentetrazole, picrotoxin, bicuculline, isoniazid or nicotine in the dose range between 10 and 1,000 mg/kg in mice, rats, golden hamsters and other mammals.

The oxindole compounds of the formula I also reduce the toxicity of strychnine in the dose range between 10 and 1,000 mg/kg. The most effective of the compounds to be used according to the invention have an efficacy superior to that of the antiepileptics currently used most frequently, and at the same time have fewer undesirable actions. The pharmacological action has been investigated in the following test models:

(1) Convulsions induced in mice by electric shock

Male mice (NMRI, Gassner) are divided into test groups of 10 animals each and pretreated with the test substance, suspended in 1% strength methylcellulose. The control group receives only the vehicle.

60 minutes after pretreatment, an electroconvulsive shock (12 mA, 50 Hz, 200 mseconds) is administered via corneal electrodes. This shock causes tonic extensor spasms in 100% of the control group. The $ED_{50}$ is the dose which prevents the tonic spasms in 50% of the animals.

In this model, 2-oxo-3-phenyl-1-indolineacetamide has an $ED_{50}$ of 214 mg/kg (0.80 mmol/kg). The antiepileptic sodium 2-propylvalerate currently used most frequently has an $ED_{50}$ of 259 mg/kg (1.80 mmol/kg) in this model.

(2) Prevention of spasms produced in mice by pentetrazole

Male mice are pretreated in test groups of 10 animals each as described under 1). 60 minutes after the pretreatment, a dose of 125 mg/kg of pentetrazole is in each case administered subcutaneously. This dose produces tonoclonic spasms in 95% of the control animals. The convulsion rate is determined during a 30 minute observation period, the animals being kept individually in glass cylinders. The $ED_{50}$ is the dose which reduces the rate of convulsions to 50%.

In this model, 2-oxo-3-phenyl-1-indolineacetamide has an $ED_{50}$ of 176 mg/kg (0.66 mmol/kg) against tonic spasms, whilst that of sodium 2-propylvalerate is 158 mg/kg (1.10 mmol/kg).

(3) Prevention of spasms produced in mice by picrotoxin

Male mice (NMRI, Gassner) are divided into test groups of 10 animals each and are pretreated as described under 1). 60 minutes after the pretreatment, a dose of 15 mg/kg of picrotoxin is in each case administered subcutaneously, producing tonoclonic convulsions in 95% of the control animals. The number of convulsions in the individual animals is determined over a 30 minute observation period. The $ED_{50}$ is the dose which reduces the number of convulsions by 50% in comparison with the control group. In this model, 2-oxo-3-phenyl-indolineacetamide has an $ED_{50}$ of 78.6 mg/kg (0.30 mmol/kg), whilst that of sodium 2-propylvalerate is 75.4 mg/kg (0.52 mmol/kg).

(4) Prevention of spasms induced in mice by bicuculline

The experiment was carried out by the method described in 3), but the picrotoxin was replaced by 5 mg/kg of bicuculline subcutaneously.

In this model, 2-oxo-3-phenyl-1-indolineacetamide has an $ED_{50}$ of 426 mg/kg (1.60 mmol/kg), whilst that of sodium 2-propylvalerate is 362 mg/kg (2.51 mmol/kg).

(5) Prevention of the spasms caused in mice by isoniazide

The experiment is carried out by the method described in 3), but picrotoxin is replaced by 600 mg/kg of isoniazid subcutaneously.

In this experiment, 2-oxo-3-phenyl-1-indolineacetamide has an $ED_{50}$ of 500 mg/kg (1.88 mmol/kg), whilst that of sodium 2-propylvalerate is 494 mg/kg (3.43 mmol/kg).

(6) Prevention of the spasms produced in mice by nicotine

The experiment is carried out by the method described in 3), but picrotoxin is replaced by 1 mg/kg of nicotine subcutaneously. Moreover, the mortality in the 30 minute observation phase is determined. The $ED_{50}$ here is the dose which reduces the lethality by 50%.

In this model, 2-oxo-3-phenyl-indolineacetamide has an $ED_{50}$ of 118 mg/kg (sodium 2-propylvalerate: 168 mg/kg) in respect of the convulsions and 119 mg/kg (sodium 2-propylvalerate: 186 mg/kg) in respect of the lethality.

(7) Prevention of the strychnine lethality in mice

The pretreatment was as described under 1). 60 minutes after the pretreatment, a dose of 2 mg/kg of strychnine was administered subcutaneously, killing 95% of the animals in the control group. The mortality was determined in a 30 minute observation period. The $ED_{50}$ is the dose which reduces the mortality by 50%.

In this experiment, 2-oxo-3-phenyl-1-indolineacetamide has an $ED_{50}$ of 376 mg/kg (1.41 mmol/kg), whilst that of sodium 2-propylvalerate is 307 mg/kg (2.13 mmol/kg).

(8) Prevention of the spasms caused in golden hamsters by pentetrazole

The experiment is carried out by a method analogous to that described under 2), but instead of the mice, 10 golden hamsters (HOECHST breeding colony) are used per test group.

In this model, 2-oxo-3-phenyl-1-indolineacetamide has an $ED_{50}$ of 127 mg/kg (0.48 mmol/kg), whilst that of sodium 2-propylvalerate is 536 mg/kg (3.7 mmol/kg).

(9) Prevention of the spasms triggered off in rats by electric shock

The experimental procedure corresponds to that described under 1), but, instead of the mice, male rats (Wistar, Ivanovas, 6–10 per test group) were used.

The electroconvulsive shock used here had the following characteristics: 30 mA, 50 Hz, 200 mseconds.

In this model, 2-oxo-3-phenyl-1-indolineacetamide has an $ED_{50}$ of 364 mg/kg (1.37 mmol/kg), whilst that of sodium 2-propylvalerate is 450 mg/kg (3.13 mmol/kg).

(10) Duration of action against spasms triggered off in mice by electric shock 160 male mice (NMRI, Ivanovas) were divided into test groups of 10 animals each. A maximum effective dose of 2-oxo-3-phenyl-1-indolineacetamide (300 mg/kg) or sodium 2-propylvalerate (500 mg/kg) was administered perorally. At various times from 0.5 to 8 hours after the pretreatment, in each case one test group was given an electric shock (12 mA, 50 Hz, 200 mseconds) via corneal electrodes, triggering off extensor spasms in 100% of the control group. The half-life is the time after which 50% of the animals are still protected from these spasms. It is more than 8 hours for 2-oxo-3-phenyl-1-indolineacetamide and 5.5 hours for sodium 2-propylvalerate.

The results described for the various experimental models suggest a powerful efficacy against epilepsy in humams.

The examples given below are intended to illustrate the preparation of suitable products for the use according to the invention.

EXAMPLE 1

Preparation of an agent used according to the invention for oral administration in the treatment of epilepsy:

1,000 tablets each containing 50 mg of 2-oxo-3-phenyl-1-indolineacetamide are prepared as follows:

| Formula | |
| --- | --- |
| 2-Oxo-3-phenyl-1-indolineacetamide | 50 g |
| Corn starch | 50 g |
| Gelatin | 40 g |
| Microcrystalline cellulose | 50 g |
| Magnesium stearate | 10 g |

2-Oxo-3-phenyl-1-indolineacetamide is mixed with a gelatin solution and the mixture is dried and ground to granules. Corn starch, microcrystalline cellulose and magnesium stearate are mixed with the granules. 1,000 tablets which contain 50 mg of the active compound and can be used for the treatment of epilepsy are formed from the mixture.

EXAMPLE 2

Gelatin capsules each containing 100 mg of 2-oxo-3-phenyl-1-indolineacetamide, are prepared as follows:

A gelatin capsule is filled with in each case a mixture of 2-oxo-3-phenyl-1-indolineacetamide (100 mg), magnesium stearate (2 mg) and lactose (135 mg). The capsules can be used for peroral administration in the treatment of epilepsy.

We claim:

1. A method of treating epilepsy, which comprises administering to a host which has epilepsy an effective amount of a compound of the formula I

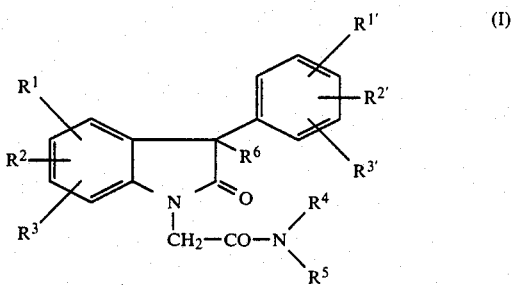

in which
  $R^1$, $R^2$, $R^3$, $R^{1'}$, $R^{2'}$ and $R^{3'}$ are identical or different and independently of one another denote hydrogen, halogen or straight-chain or branched alkyl with 1 to 4 carbon atoms,
  $R^4$ and $R^5$ are identical or different and independently of one another denote hydrogen or straight-chain or branched alkyl with 1 to 4 carbon atoms; cyclohexyl, alkylcyclohexyl with 1 to 4 carbon atoms in the alkyl part, cycloheptyl or cyclooctyl; phenyl, which can be mono- or di-substituted by halogen, straight-chain or branched alkyl with 1 to 4 carbon atoms, trifluoromethyl, methylenedioxy or alkoxy with 1 to 3 carbon atoms; or phenylalkyl with 1 to 3 carbon atoms in the alkyl part, it being possible for the phenyl nucleus to be substituted as indicated above for phenyl, or hydroxyalkyl with 1 to 4 carbon atoms, or $R^4$ and $R^5$, together with the nitrogen atom carrying them, denote pyrrolidino, piperidino, morpholino or phenylpiperazino, it being possible for the phenyl nucleus to be substituted as indicated above for phenyl, and
  $R^6$ denotes hydrogen, alkyl with 1, 2 or 3 carbon atoms or hydroxyl,
  or a physiologically acceptable salt thereof.

2. A method of treating epilepsy, which comprises administering to a host which has epilepsy an effective amount of 2-oxo-3-phenyl-1-indolineacetamide.

3. A method of treating epilepsy as claimed in claim 1 in which, in the compound of the formula I,
  $R^{1'}$, $R^{2'}$ and $R^{3'}$ denote hydrogen,
  $R^1$ denotes hydrogen or chlorine in the 5-position of the indole,
  $R^2$ and $R^3$ denote hydrogen,
  $R^4$ and $R^5$ are identical or different and independently of one another denote hydrogen, alkyl with 1, 2 or 3 carbon atoms, cyclohexyl, methylcyclohexyl, cycloheptyl, cyclooctyl, hydroxyalkyl with 2 or 3 carbon atoms or benzyl or phenethyl, it being possible for the phenyl radicals in each case to be mono- or di-substituted in the phenyl nucleus by halogen, such as fluorine or chlorine, methylenedioxy or alkoxy with 1, 2 or 3 carbon atoms, or $R^4$ and $R^5$, together with the nitrogen atom carrying them, denote piperidino, pyrrolidino, morpholino or N-phenylpiperazino, it being possible for the phenyl nucleus to be mono- or di-substituted by fluorine or chlorine, methylenedioxy or alkoxy with 1, 2 or 3 carbon atoms, and
  $R^6$ denotes hydrogen, methyl or hydroxyl.

* * * * *